(12) United States Patent
Hsieh et al.

(10) Patent No.: US 7,254,259 B2
(45) Date of Patent: Aug. 7, 2007

(54) METHODS AND APPARATUS FOR TRUNCATION COMPENSATION

(75) Inventors: Jiang Hsieh, Brookfield, WI (US); Brian Grekowicz, Waukesha, WI (US); Edward Henry Chao, Oconomowoc, WI (US); Scott Matt McOlash, Wauwatosa, WI (US); Amy Lynn Horst, Hartford, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 937 days.

(21) Appl. No.: 10/615,411

(22) Filed: Jul. 3, 2003

(65) Prior Publication Data

US 2004/0073584 A1 Apr. 15, 2004

Related U.S. Application Data

(60) Provisional application No. 60/416,072, filed on Oct. 4, 2002.

(51) Int. Cl.
*G06K 9/00* (2006.01)

(52) U.S. Cl. .................................................... 382/131

(58) Field of Classification Search ................ 382/128, 382/131–133; 250/363.04
See application file for complete search history.

(56) References Cited

U.S. PATENT DOCUMENTS

| | | | |
|---|---|---|---|
| 4,136,388 A | 1/1979 | Lindquist | |
| 4,189,775 A | 2/1980 | Inouye et al. | |
| 4,305,127 A | 12/1981 | Heuscher | |
| 4,446,521 A | 5/1984 | Inouye | |
| 4,550,371 A | 10/1985 | Glover et al. | |
| 4,878,169 A | 10/1989 | Toner et al. | |
| 5,043,890 A | 8/1991 | King | |
| 5,276,614 A | 1/1994 | Heuscher | |
| 5,640,436 A | 6/1997 | Kawai et al. | |
| 5,953,388 A | 9/1999 | Walnut et al. | |
| 6,307,909 B1 | 10/2001 | Flohr et al. | |
| 6,549,646 B1 * | 4/2003 | Yeh et al. | 382/132 |
| 6,810,102 B2 * | 10/2004 | Hsieh et al. | 378/4 |
| 6,856,666 B2 * | 2/2005 | Lonn et al. | 378/8 |

OTHER PUBLICATIONS

US 5,299,248, 03/1994, Pelc (withdrawn)

* cited by examiner

*Primary Examiner*—Vikkram Bali
(74) *Attorney, Agent, or Firm*—Armstrong Teasdale LLP (57) ABSTRACT

A method includes calculating a sum of all samples at each projection view of a scan of an object, determining a maximum value of the calculated sums, averaging a plurality of samples m at a projection view index k when the sum of all samples at index k is less than a predetermined percentage of the maximum value, comparing the average to a threshold t, determining the projection truncated when the average is greater than t, and determining the projection not truncated when the average is not greater than t.

27 Claims, 5 Drawing Sheets

METHODS AND APPARATUS FOR TRUNCATION COMPENSATION

CROSS REFERENCE TO RELATED APPLICATIONS

This application claims the benefit of U.S. provisional application No. 60/416,072 filed Oct. 4, 2002, which is hereby incorporated in its entirety.

BACKGROUND OF THE INVENTION

This invention relates generally to methods and apparatus for computed tomographic (CT) image reconstruction, and more particularly to methods and apparatus that provide for truncation compensation.

Under some scanning conditions, portions of a patient may extend beyond a region measured by a detector, which may lead to image artifacts and an incomplete representation of the imaged object. Some known methods have been published that address artifact reductions but not the imaging of the portion of the patient that is outside the field of view (FOV). However, it is desirable to image the portion of the patient that extends beyond the FOV such as is described in copending application Ser. No. 10/602,565 titled Methods and Apparatus for Truncation Compensation, and filed on Jun. 24, 2003 with Ser. No. 10/602,565 (which is also hereby incorporated in its entirety), and claiming the benefit of provisional application Ser. No. 60/416,072 filed Oct. 4, 2002. Additionally, it is desirable to increase image quality of portions of the patient that extend beyond the FOV.

BRIEF DESCRIPTION OF THE INVENTION

In one aspect, a method for determining whether a projection is truncated is provided. The method includes calculating a sum of all samples at each projection view of a scan of an object, determining a maximum value of the calculated sums, averaging a plurality of samples m at a projection view index k when the sum of all samples at index k is less than a predetermined percentage of the maximum value, comparing the average to a threshold t, determining the projection truncated when the average is greater than t, and determining the projection not truncated when the average is not greater than t.

In another aspect, an imaging apparatus is provided. The imaging apparatus includes a radiation source, a detector responsive to radiation positioned to receive radiation emitted from the source, and a computer operationally coupled to the radiation source and the detector. The computer is configured to calculate a sum of all samples at each projection view of a scan of an object, determine a maximum value of the calculated sums, average a plurality of samples m at a projection view index k when the sum of all samples at index k is less than a predetermined percentage of the maximum value, compare the average to a threshold t, determine the projection truncated when the average is greater than t, and determine the projection not truncated when the average is not greater than t.

In a further aspect, a computer readable medium is provided which is encoded with a program configured to instruct a computer to calculate a sum of all samples at each projection view of a scan of an object, determine a maximum value of the calculated sums, average a plurality of samples m at a projection view index k when the sum of all samples at index k is less than a predetermined percentage of the maximum value, compare the average to a threshold t, determine the projection truncated when the average is greater than t, determine the projection not truncated when the average is not greater than t, and estimate a total attenuation $\tau(k)$ in accordance with $\tau(k)=k_2-k/k_2-k_1 \xi(k_1)+ k-k_1/k_2-k_1 \xi(k_2)$ where of a plurality of view locations of un-truncated views adjacent to a truncation region comprising at least one projection determined truncated, and $\xi(k)$ is calculated as $$\xi(k) = \sum_{i=1}^{N} p(i, k).$$

The program is further configured to instruct the computer to determine a attenuation difference $\lambda(k)$ in accordance with $\lambda(k)=\tau(k) -\xi(k)$, calculate an amount of attenuation to add $\eta(k)$ in accordance with $$\eta(k) = \frac{\pi}{2} R_l^2(k) - x_l(k) p_l(k) - R_l^2(k)\arcsin\left(\frac{x_l(k)}{R_l(k)}\right) + \frac{\pi}{2} R_r^2(k) - x_r(k) p_r(k) - R_r^2(k)\arcsin\left(\frac{x_r(k)}{R_r(k)}\right)$$

where $p_l(k)$, and $p_r(k)$, are the magnitude of a left and a right projection boundary samples averaged over multiple views, respectively, and $x_l(k)$, $x_r(k)$, $R_l(k)$, and $R_r(k)$ are a location and radius of a left and right fitted cylinders, respectfully, compare $\eta(k)$ to $\lambda(k)$ by calculating a ratio $$\varepsilon(k) = \frac{\eta(k)\mu_w}{\lambda(k)}$$

where $\mu_w$ is an attenuation coefficient of water, compare $\epsilon(k)$ to a threshold q, and use at least one of $\eta(k)$ and $\lambda(k)$ to correct an image when $\epsilon(k)$ is not greater than q. The program is further configured to instruct the computer, when $\epsilon(k)$ is greater than q, to calculate a $\eta_n(k)$ based on data regarding a $k_1-n$ view and a $k_2+n$ view, wherein n is an integer, and correct an image using the $\eta_n(k)$.

DETAILED DESCRIPTION OF THE INVENTION

There is herein provided truncation compensation methods and apparatus for Extended Field-of-View in Computed Tomography Systems. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 1:
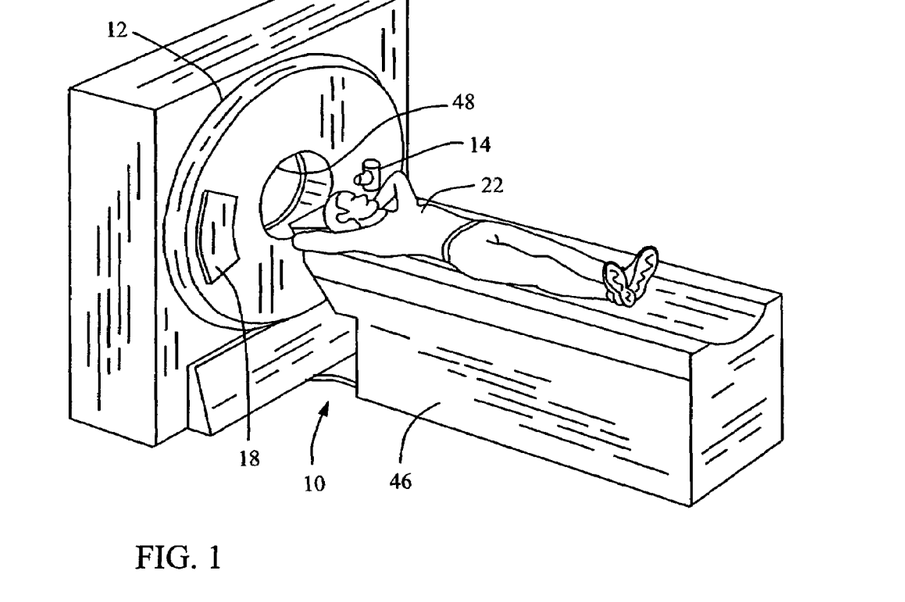
FIG. 1 is a pictorial view of a CT imaging system embodiment.
Figure 2:
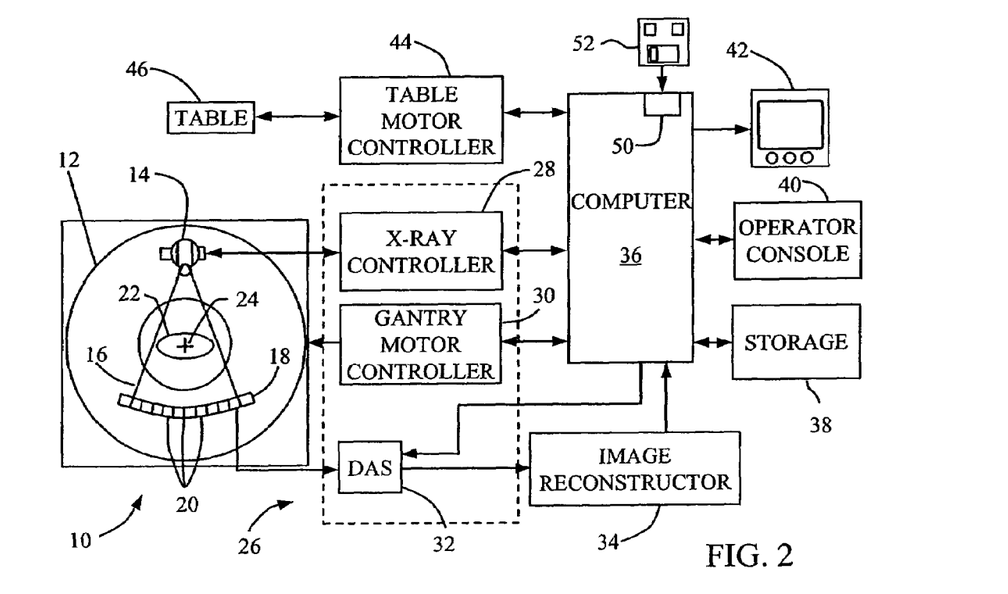
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

Some known methods have been published that address the artifact reduction but not the imaging of a portion of patient 22 that is outside a field of view (FOV). However, it is desirable to image the portion of the patient that extends beyond the FOV. This is useful in many fields including Oncology, Spin Angiography, Fused imaging systems, and in Economy CT Scanners. The current hardware of at least one known multi-slice CT scanner limits the reconstruction field of view (FOV) to about 50 centimeters (cm.). Although this is sufficient for most clinical applications, it is desirable to expand the FOV to image objects outside this FOV. This may have particular advantages for applications such as oncology or CT/PET. For oncology applications, a larger FOV is desired. This is mainly due to the fact that for radiation treatment planning, the limbs of the patient are often positioned outside the scan FOV for better tumor positioning. The known CT reconstruction algorithms ignore the truncated projections and produce images with severe artifacts. These artifacts may affect an accurate estimation of the attenuation path for treatment planning. Herein described is an algorithmic approach to increase the reconstruction FOV beyond the FOV limited by the detector hardware. This correction algorithm can be applied to various reconstruction algorithms including, but not limited to, Full scans, Halfscan/segment, helical scan, and cardiac sector based algorithms. Additionally, system 10 is configured to employ the herein described algorithms.

Figure 3:
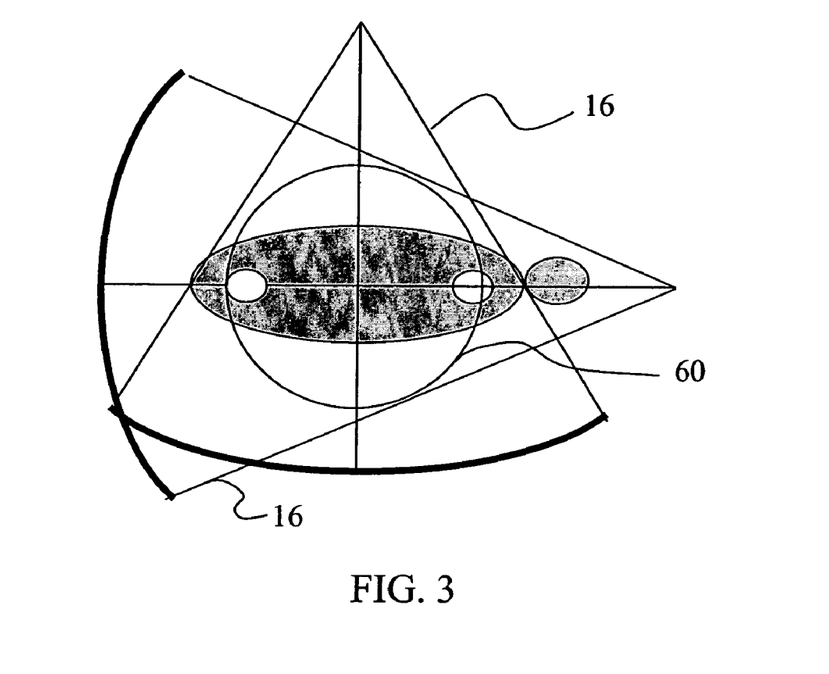
FIG. 3 illustrates a projection truncation occurring only in a portion of the projection angles.

FIG. 3 illustrates a projection truncation occurring only in a portion of the projection angles. Under some scanning conditions, portions of patient 22 extend beyond the region measured by detector 18, which may lead to image artifacts and an incomplete representation of the imaged object. The X-ray tube and detector 18 are rigidly held together on a frame which rotates around patient 22. During the course of rotation, measurements are continuously made within a "filly sampled field of view" 60. The attenuation of x-rays traversing any areas of object 22 positioned outside fully sampled field of view 60 is measured at a limited range of rotation angles, and this region is referred to as the "partially sampled field of view" region. In other words, portions that are within fully sampled field of view 60 are positioned within fan 16 such that measurements are obtainable at all gantry angles, and the data collected is defined as filly sampled field of view data. Some portions, however, are within fan 16 at some angles but are outside fan 16 at other angles, and the data collected regarding these portions is defined as partially sampled field of view data. In this example, the projection taken at a 3 o'clock position is free of truncation and the projection taken at a 12 o'clock is severely truncated. Therefore, one can rely on the un-truncated projections (i.e., positions around 3 o'clock in FIG. 3, for example) to estimate the amount of truncation for the truncated views (e.g., positions around 12 o'clock for the example in FIG. 3). One early step in the correction process is to perform software fan-beam to parallel-beam rebinning on the pre-processed projections. In one embodiment, that early step is the first step. This process is well known in the art and does not require special data collection. Once the rebinning is completed, the projections are integrated over all detector channels to obtain a total attenuation curve as described in more detail below.

Figure 4:
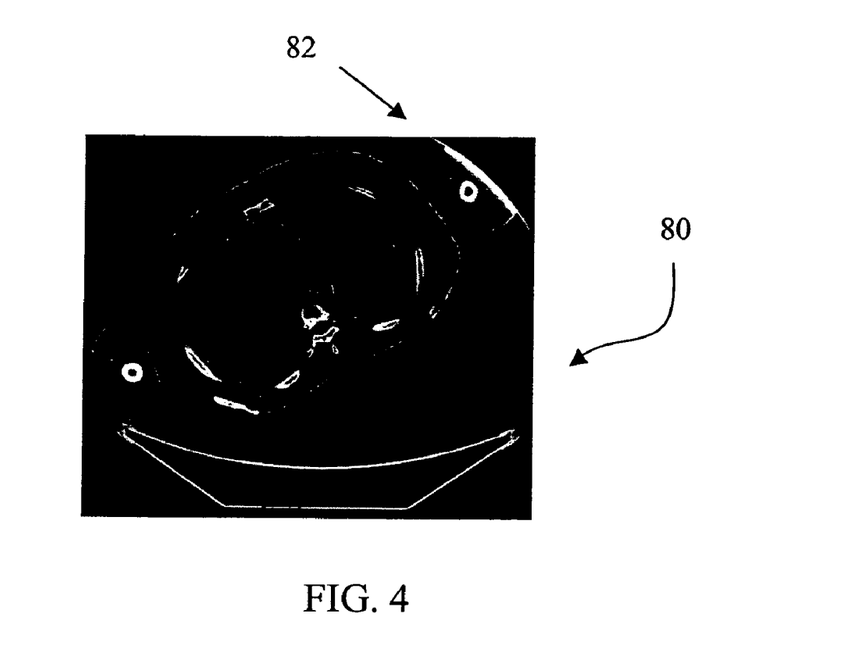
FIG. 4 illustrates a reconstructed image in which no truncation correction was performed.

FIG. 4 illustrates a reconstructed image 80 in which no truncation correction was performed. As is easily observed, image 80 contains truncation artifacts 82.

Figure 5:
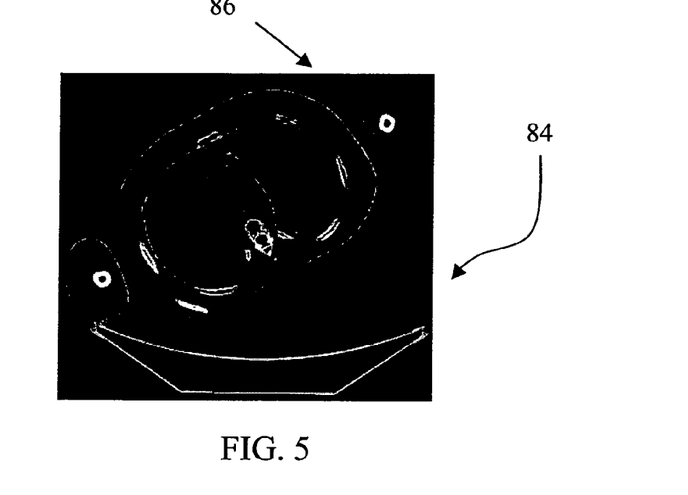
FIG. 5 illustrates an image with truncation correction as described in Ser. No. 10/602,565.

Ser. No. 10/602,565 describes an algorithm that enables truncation compensation for a majority of situations. Under certain conditions, however, the compensation algorithm described in attorney docket number 129993 does not produce optimal results. FIG. 5 illustrates an image 84 with truncation correction as described in Ser. No. 10/602,565. Although image 84 illustrates much improvement over image 80, image 84 has distortion in a corrected area 86 (restored arm). In this example, a chest phantom was positioned so that an outermost region is 29 cm from iso-center (at the edge of a 58 cm FOV). Although the previous correction removes the artifacts inside the 50 cm FOV, the shape and intensity of the restored arm 86 is somewhat distorted.

It is believed that the distortion is caused mainly by an inaccuracy in the estimation of the missing attenuation. For illustration, a total amount of measured attenuation 90 of each projection is plotted as a function of projection view in FIG. 6. For clarity, the graph is plotted on an expanded scale. A plurality of dips 92 in measured attenuation 90 correspond to truncated views. It is clear from the graph that the summation of the measured projection measurement for each projection is not a constant over projection angles for a plurality of non-truncated projections (areas of measured attenuation 90 which are approximately flat). This is due to a non-ideal calibration and the fan-parallel rebinning process. Although the variation is small (less than 2%), it could represent a significant portion of the total truncated projection samples. In other words, as compared to the estimated missing projection, the variation percentage is much larger. Therefore, using additional information for the truncation estimation than used in the compensation described in Ser. No. 10/602,565 will result in less or no distortion.

During a plurality of phantom experiments, it was found that the magnitude and slope at the projection boundary alone are sometimes insufficient for the estimation of the size and location of a cylindrical object to be fitted in to the projection because sometimes the slope of the boundary sample(s) is biased by an internal structure of the scanned object. For example, if an air pocket happens to be located tangential to a truncated projection boundary sample, significant discontinuity (in projection angle) in the extrapolated projection samples can result. This could lead to shading and streaking artifacts.

Another complication occurs when the projection samples are noisy (due to limited x-ray photon statistics). Under this condition, both the magnitude and slope of the projection boundary may become unreliable. High frequency variations (from view to view) may result in severe streaks and highly distorted object shapes. Clinically, this can occur when a large patient is scanned or when a low-flux acquisition protocol is used. The herein described methods and apparatus at least partially overcome these above described difficulties.

More specifically, projections are declared either truncated or non-truncated (i.e., un-truncated). To declare (i.e., determine) a projection as truncated, a condition is imposed that either side of the projection boundary samples (averaged over a few channels) has to be less than a predetermined threshold in addition to the previously imposed conditions identified in Ser. No. 10/602,565. The average of plurality of samples should be an average of plurality of edge samples. That is, if the projection contains N samples indexed from 0 to N−1, the average of the left m projection samples from 0 to m−1, and the average of the right m samples from N−m to N−1 are used. In addition to the above test, the test in Ser. No. 10/602,565 is still used. That is, the sum of all N samples is calculated for all views. The maximum value over all projection views is calculated, and when the sum of a particular view is less than a predetermined percentage of the maximum value, this view is declared truncated. The threshold value is non-zero to account for the non-ideal calibrations. Mathematically, a projection is declared truncated if the following condition exists $$p_l = \frac{1}{m}\sum_{i=1}^{m} p(i,k) > t, \text{ or } p_r = \frac{1}{m}\sum_{i=1}^{m} p(N-i,k) > t \quad (1)$$

where N is the number of detector channels, k is the projection view index, m is the number of samples, and t is the value of the threshold. In an exemplary embodiment, t equal to about 0.42 has empirically shown to provide a good performance. In other embodiments, t is between about 0.25 and 0.58, t is between about 0.33 and 0.5, and/or t is between about 0.375 and 0.46.

Figure 6:
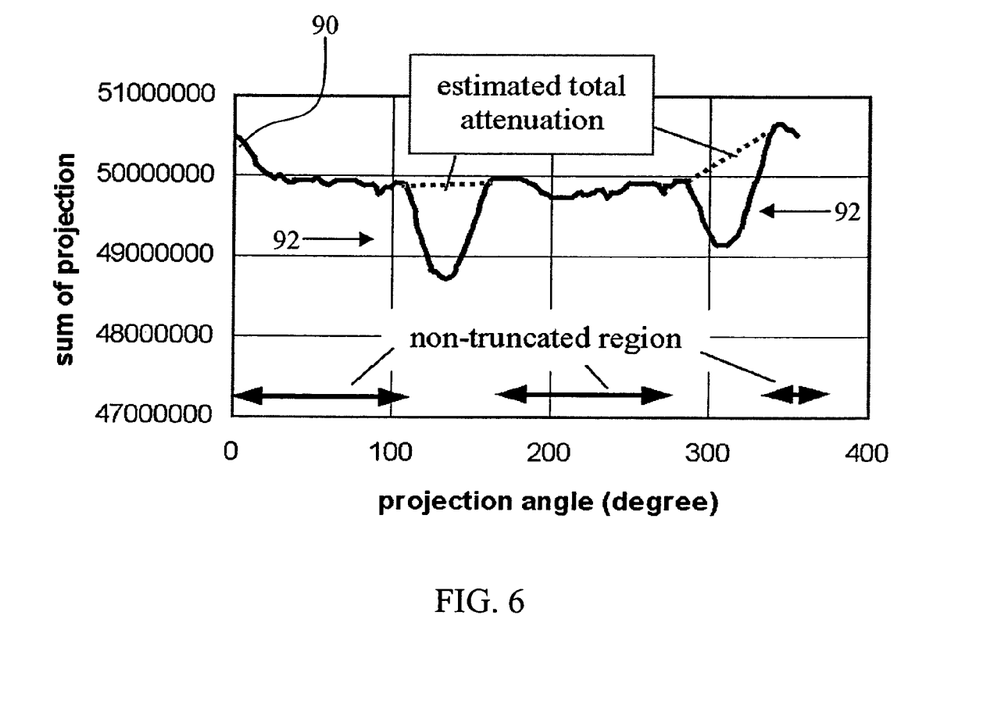
FIG. 6 is a graph of a total amount of measured attenuation of each projection plotted as a function of projection view.

Using this above described determination method, the non-truncated views are identified as shown with double arrows in FIG. 6. To estimate the amount of missing projections, the total attenuations of neighboring un-truncated projections are used for the estimation. In specific, the total attenuation of the truncated view is obtained by linearly interpolating the two un-truncated projections on both sides of the truncation view region. For the example shown in FIG. 6, the first set of truncated views is located between projection view number 290 (106° in terms of projection angle) and 445 (163° in terms of projection angle). The total attenuation obtained for view number 289 and 446 is used to estimate the total attenuation of the truncated views. The estimation is performed by linearly interpolating the two un-truncated samples, as shown by dotted lines in FIG. 6. Mathematically, the estimated total attenuation, τ(k), is then $$\tau(k) = \frac{k_2 - k}{k_2 - k_1}\xi(k_1) + \frac{k - k_1}{k_2 - k_1}\xi(k_2) \quad (2)$$

where $k_1$ and $k_2$ are the view locations of the un-truncated views adjacent to the truncation region. ξ(k) is the total attenuation obtained by summing up the projection measurement for view k. Mathematically, it is described by the following equation $$\xi(k) = \sum_{i=1}^{N} p(i,k) \quad (3)$$

To improve the robustness of the algorithm, one can use the average of several projection views for the un-truncated projections. For example, one could use the average total attenuation of views 285 to 289 instead of the view 289 alone, and $k_1$ then refers to the average values for views 285 to 289. In an exemplary embodiment, the average is taken over five views, but in other embodiments, the average is taken over a number of views other than five (e.g., 3-7 views, and 2-8 views). Additionally, $k_2$ can refer to a single view or an average of several view independent of $k_1$. For example, and referring the to example shown in FIG. 6, let $k_1$ refer to the average values of views 285 to 289, then, in one embodiment, $k_2$ refers to the average values of views 446-450, and, in another embodiment, $k_2$ refers to 446. Additionally, $k_1$ is independent of $k_2$, and $k_1$ can refer to a single view or multiple views regardless of $k_2$.

An additional amount of projection needed to make up for the truncation, λ(k), is then the difference between estimated total attenuation and the measured total attenuation $$\lambda(k) = \tau(k) - \xi(k) \quad (4)$$

Figure 7:
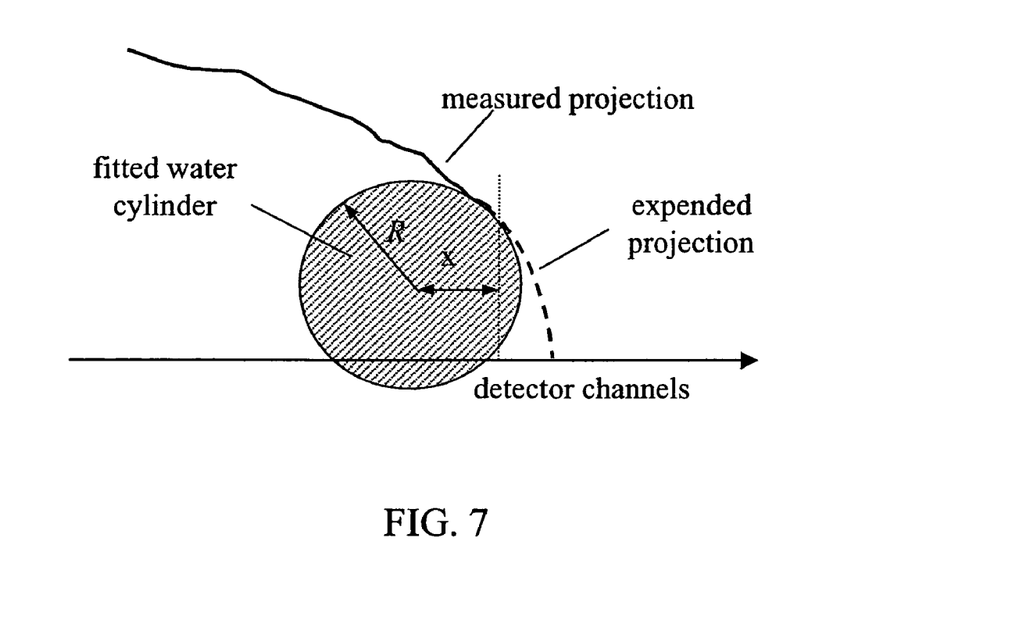
FIG. 7 graphically describes a fitting process.

Next, a size and a location of a water cylindrical object that can be fitted at the boundaries of each truncated projection are estimated to come up with an estimated projection. The location and the radius of the fitted cylinder is calculated based on the magnitude and the slope of the truncated projection boundary samples averaged over m projection views $$x_l(k) = \frac{-s_l(k)p_l(k)}{4\mu_w^2}, \text{ and } R_l(k) = \sqrt{\frac{p_l^2(k)}{4\mu_w^2} + x_l^2(k)} \quad (5)$$

$$x_r(k) = \frac{-s_r(k)p_r(k)}{4\mu_w^2}, \text{ and } R_r(k) = \sqrt{\frac{p_r^2(k)}{4\mu_w^2} + x_r^2(k)} \quad (6)$$

where $p_l$, $s_l$, $p_r$, and $s_r$ are the magnitude and slopes of the left and right projection boundary samples averaged over multiple views, respectively, and $x_l$, $x_r$, $R_l$, and $R_r$ are the location and radius of the left and right fitted cylinders, respectfully, and $\mu_w$ is the attenuation coefficient of water. The fitting process is described graphically in FIG. 7.

Figure 8:
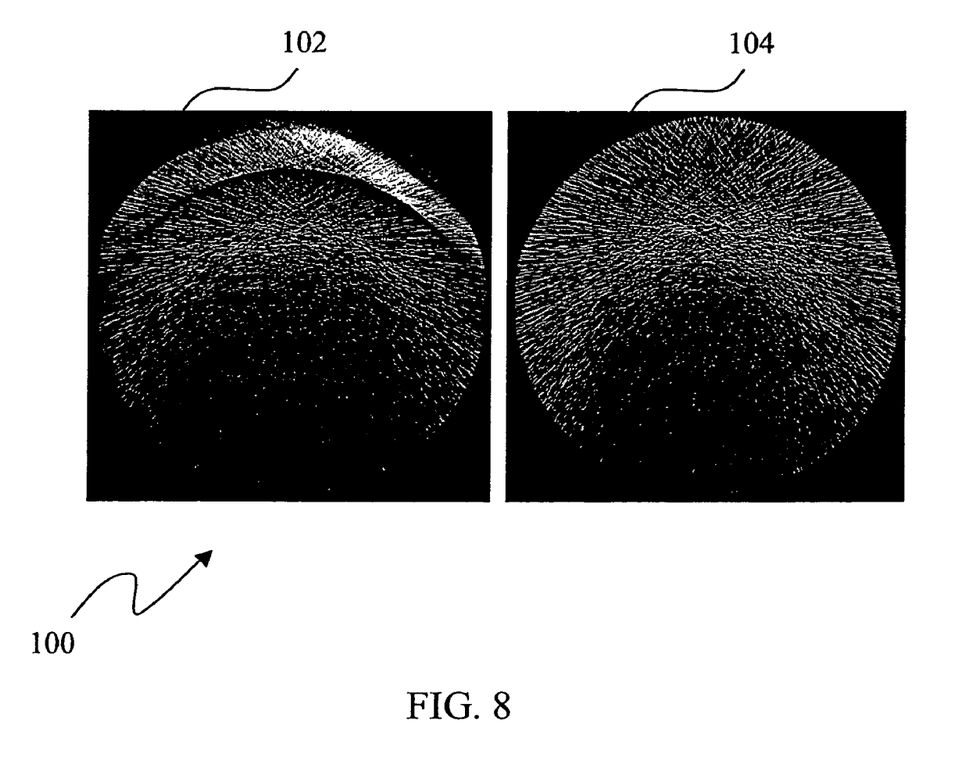
FIG. 8 illustrates a plurality of images including an image where only a single view was used to estimate the magnitude and the slope of the left truncated projections, $p_l$, $s_l$, and a single view was used to estimate the magnitude and the slope of the right truncated projections $p_r$, and $s_r$.

Previously, it was indicated that under x-ray photon starvation conditions, the parameter estimation process might become unreliable because the estimated parameters may fluctuate significantly from view to view. FIG. 8 illustrates a plurality of images 100 including an image 102 where only a single view was used to estimate the magnitude and the slope of the left truncated projections, $p_l$, $s_l$, and a single view was used to estimate the magnitude and the slope of the right truncated projections $p_r$, and $s_r$. Image 102 clearly illustrates streaking artifacts caused by parameter fluctuation. To overcome this possible shortcoming, the use of projection samples averaged over several views is employed, in one embodiment, to estimate the magnitude and the slope of the truncated projections, $p_l$, $s_l$, $p_r$, and $s_r$. In an exemplary embodiment, projection samples of seven views are used for the slope and magnitude estimation. Plurality of images 100 also includes an averaged image 104 is which seven views were used for the slope and magnitude estimation. In another embodiment, between 5 and 9 views inclusive are used for the slope and magnitude estimation. The averaged values are then used for the radius and location determination of the fitted cylinders. Based on the fitted cylinders, the total amount of attenuation of the added cylinders for projection k, η(k), (the portion of the cylinder that extends beyond the original projection) is calculated based on the following formula $$\eta(k) = \frac{\pi}{2} R_l^2(k) - x_l(k) p_l(k) - R_l^2(k) \arcsin\left(\frac{x_l(k)}{R_l(k)}\right) + \frac{\pi}{2} R_r^2(k) - x_r(k) p_r(k) - R_r^2 \arcsin\left(\frac{x_r(k)}{R_r(k)}\right) \quad (7)$$

In one embodiment, this quantity is checked against the estimated amount of additional attenuation, λ(k), described in Eq. (4). Ideally, these two quantities should be equal. In reality, however, since the missing portion of the object is rarely a perfect cylinder, there will always be some differences between the two quantities. Therefore, the ratio of the two quantities is calculated, ε(k)

$$\varepsilon(k) = \frac{\eta(k)\mu_w}{\lambda(k)} \quad (8)$$

When the quantity, ε(k), is significantly different than unity, it potentially indicates a problem with the fitted cylindrical parameters. This could be caused by an irregular shape of the scanned object as described previously. Therefore, when ε(k)>q, one may not want to use the estimated parameters for projection compensation. q is a pre-determined threshold and is set to 2 in an exemplary embodiment. In another exemplary embodiment, q is between 1.5 and 2.5. In another embodiment, q is between 1.75 and 2.25. In another exemplary embodiment, q is between 1.9 and 2.1.

For the projections in which ε(k)>q, one may want to use interpolated values of the cylindrical parameters of two projections with a good parameter fit (i.e., ε(k)<q). That is, if ε(k) values for views $k_1$ to $k_2$ exceed the threshold, one may want to use the fitted cylinder parameters of view $k_1$−n and $k_2$+n to estimate the cylindrical parameters for these views, where n is a parameter, and n=1 indicates the first "good fit" views. In an exemplary embodiment, n=5 was selected and linear interpolation has been shown to be sufficient. That is, $x_l(k)$, $x_r(k)$, $R_l(k)$, and $R_r(k)$ are linearly interpolated based on $x_l(k_1-n)$, $x_l(k2+n)$, $x_r(k1-n)$, $x_r(k2+n)$, $R_l(k1-n)$, $R_l(k2+n)$, $R_r(k_1-n)$ and $R_r(k2+n)$, and $\eta_n(k)$ is calculated according to Eq. 7 using the interpolated values. The ratio, ε(k), is also linearly interpolated from the same set of views. Of course, other interpolation method, such as higher order interpolations, can be used. In addition, additional low-pass filtering along the view, k, can be applied to the estimated parameters to further improve the continuity of the parameters. In other embodiments, n is between 2 and 8, and/or n is between 3 and 7.

Figure 9:
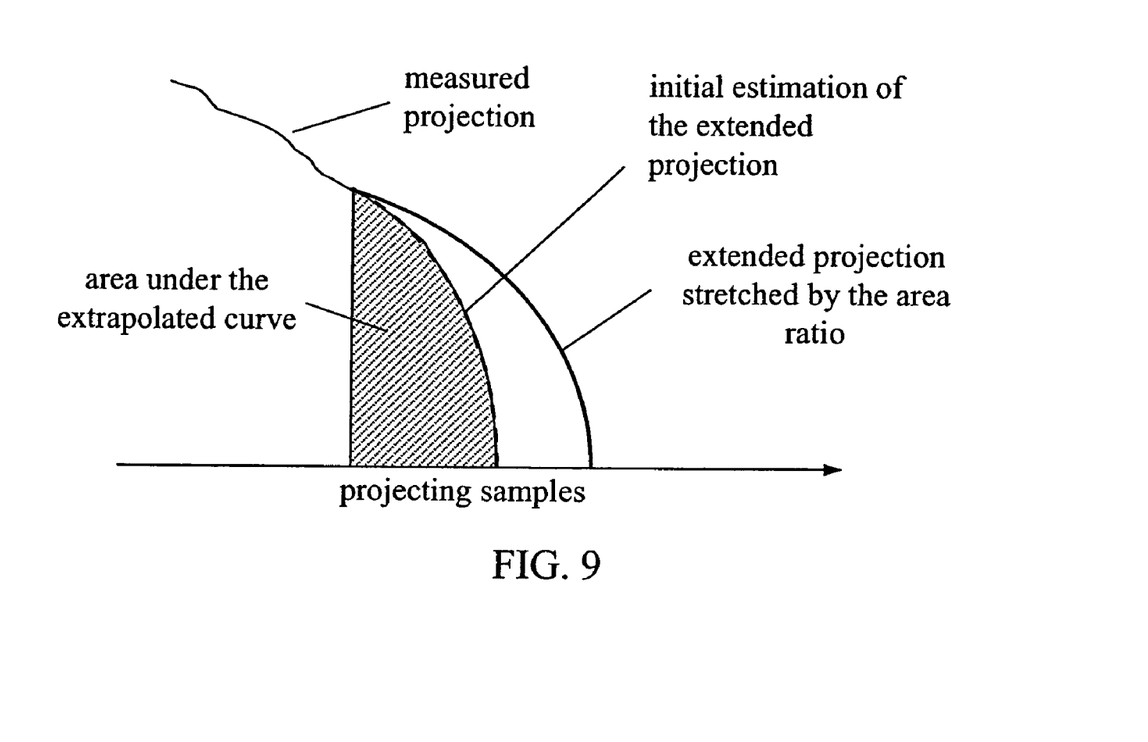
FIG. 9 graphically illustrates how missing projection samples are calculated based on the estimated cylinders.

Finally, the missing projection samples are calculated based on the estimated cylinders. FIG. 9 graphically illustrates this process. Since the total attenuation of these cylinders is unlikely to match the total missing attenuation estimated using the consistency condition (Eq. 4), additional adjustment can be used. For example, the x-axis (detector channel index i) is scaled by the ratio so that the initial estimated projection (shown by a dotted line in FIG. 9) is further expanded (shown by a solid thick line in FIG. 9) or compressed in x. This can be accomplished by changing the indexing distance of detector channel i or by interpolating the initially calculated projections.

Figure 10:
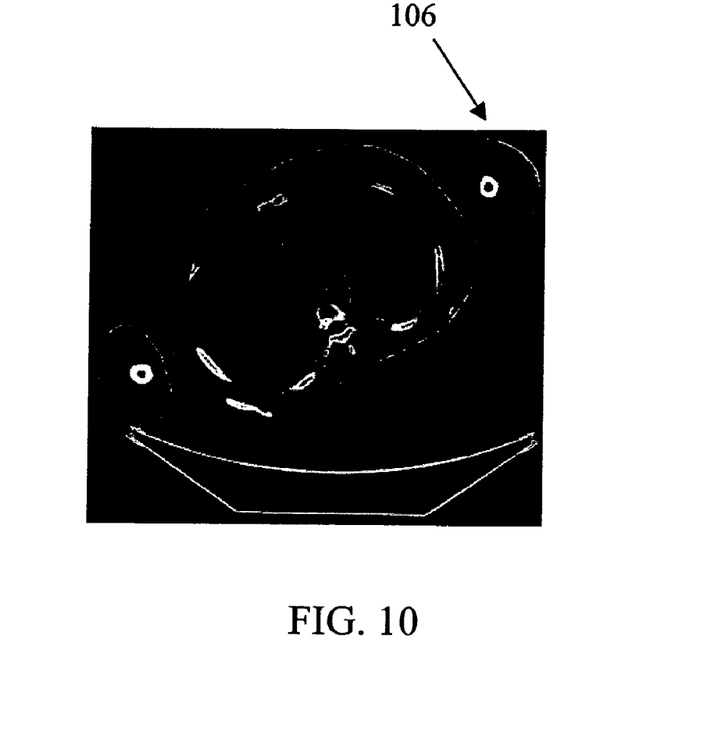
FIG. 10 shows the same phantom scan shown in FIGS. 4 and 5 corrected with the herein described methods and apparatus.

With the herein described methods and apparatus, the performance and robustness of the methods and apparatus described in Ser. No. 10/602,565 are significantly improved. FIG. 10 shows the same phantom scan shown in FIGS. 4 and 5 corrected with the herein described methods and apparatus. Improvement in the accuracy of the shape and density of an object 106 outside the scan FOV is obvious, which is one technical effect or contribution for the disclosed invention. Of course, other technical effects exist also.

Although the above described system and methods uses only the conservation of total attenuation, the magnitude, and the slope of the boundary samples to estimate the missing projection distribution, additional information can also be used for the estimation. For example, one could use the Helgason-Ludwig Condition (HL condition) for tomography to further refine the above techniques. Additionally, different thresholds can be placed to ensure that the algorithm functions properly under erroneous measurement conditions. For example, one could set the upper and lower limits on the stretch ratio described in FIG. 9 to prevent the condition of increased error due to unreliable measurement. In addition, the slope calculation of $s_1$ and $s_r$ can be set such that it falls within a reasonable range. If the characteristic of the material of the scanned object is known to be significantly different from water, one can also use the attenuation coefficients of the known material (instead of water) to perform size and location calculations shown in Eqs. (3) and (4).

Because the interpolated data may not have the same image quality as data within the fully sampled FOV it may be useful to tag the image where the FOV becomes extrapolated. In one embodiment, a delineation is provided in a reconstructed image between areas representative of the fully sampled field of view data and the partially sampled field of view data. This could also be done with a color code or shift in the CT Number. Because the tag may impact the ability to view the image data an easy way is provided to turn on and off the tagging. And therefore, a user of system 10 is allowed to turn on or off the tagging.

While the invention has been described in terms of various specific embodiments, those skilled in the art will recognize that the invention can be practiced with modification within the spirit and scope of the claims.

What is claimed is:

1. A method for determining whether a projection is truncated, said method comprising:
    calculating a sum of all samples at each projection view of a scan of an object;
    determining a maximum value of the calculated sums;
    averaging a plurality of samples m at a projection view index k when the sum of all samples at index k is less than a predetermined percentage of the maximum value;
    comparing the average to a threshold t;
    determining the projection truncated when the average is greater than t; and
    determining the projection not truncated when the average is not greater than t.

2. A method in accordance with claim 1 further comprising augmenting partially sampled field of view data using fully sampled field of view data when the projection is determined truncated.

3. A method in accordance with claim 1 wherein said comparing the average to a threshold t comprises comparing the average to a threshold t, wherein t is between about 0.25 and about 0.58.

4. A method in accordance with claim 3 wherein said comparing the average to a threshold t comprises comparing the average to a threshold t, wherein t is between about 0.33 and about 0.5.

5. A method in accordance with claim 4 wherein said comparing the average to a threshold t comprises comparing the average to a threshold t, wherein t is between about 0.375 and about 0.46.

6. A method in accordance with claim 5 wherein said comparing the average to a threshold t comprises comparing the average to a threshold t, wherein t is about 0.42.

7. A method in accordance with claim 1 further comprising estimating a total attenuation $\tau(k)$ using a plurality of projection views.

8. A method in accordance with claim 7 wherein said estimating a total attenuation $\tau(k)$ using a plurality of projection views comprises estimating a total attenuation $\tau(k)$ in accordance with:

$$\tau(k) = \frac{k_2 - k}{k_2 - k_1}\xi(k_1) + \frac{k - k_1}{k_2 - k_1}\xi(k_2)$$

where $k_1$ and $k_2$ are view locations of un-truncated views adjacent to a truncation region comprising at least one projection determined truncated, and $\xi(k)$ is calculated as $$\text{as } \xi(k) = \sum_{i=1}^{N} p(i, k).$$

9. A method in accordance with claim 8 further comprising determining an attenuation difference $\lambda(k)$ in accordance with $\lambda(k)=\tau(k)-\xi(k)$.

10. A method in accordance with claim 9 further comprising:
calculating an amount of attenuation to add $\eta(k)$ in accordance with $$\eta(k) = \frac{\pi}{2}R_l^2(k) - x_l(k)p_l(k) - R_l^2(k)\arcsin\left(\frac{x_l(k)}{R_l(k)}\right) + \frac{\pi}{2}R_r^2(k) - x_r(k)p_r(k) - R_r^2\arcsin\left(\frac{x_r(k)}{R_r(k)}\right)$$

where $p_l(k)$, and $p_r(k)$, are the magnitude of a left and a right projection boundary samples averaged over multiple views, respectively, and $x_l(k)$, $X_r(k)$, $R_1(k)$, and $R_r(k)$ are a location and radius of a left and right fitted cylinders, respectfully; and
comparing $\eta(k)$ to $\lambda(k)$.

11. A method in accordance with claim 10 wherein said comparing $\eta(k)$ to $\lambda(k)$ comprises calculating a ratio $$\varepsilon(k) = \frac{\eta(k)\mu_w}{\lambda(k)}$$

where $\mu_w$ is an attenuation coefficient of water, said method further comprising:
comparing $\epsilon(k)$ to a threshold q; and
using at least one of $\eta(k)$ and $\lambda(k)$ to correct an image when $\epsilon(k)$ is not greater than q; and
not using either of $\eta(k)$ and $\lambda(k)$ to correct an image when $\epsilon(k)$ is greater than q.

12. A method in accordance with claim 11 wherein said comparing $\epsilon(k)$ to a threshold q comprises comparing $\epsilon(k)$ to a threshold q, wherein q is between about 1.5 and about 2.5.

13. A method in accordance with claim 11 wherein said comparing $\epsilon(k)$ to a threshold q comprises comparing $\epsilon(k)$ to a threshold q, wherein q is between about 1.75 and about 2.25.

14. A method in accordance with claim 11 wherein said comparing $\epsilon(k)$ to a threshold q comprises comparing $\epsilon(k)$ to a threshold q, wherein q is between about 1.9 and about 2.1.

15. A method in accordance with claim 11 wherein said comparing $\epsilon(k)$ to a threshold q comprises comparing $\epsilon(k)$ to a threshold q, wherein q is about 2.

16. A method in accordance with claim 11 wherein said using at least one of $\eta(k)$ and $\lambda(k)$ to correct an image when $\epsilon(k)$ is not greater than q comprises using $\eta(k)$ to correct an image when $\epsilon(k)$ is not greater than q.

17. A method in accordance with claim 11 wherein said not using either of $\eta(k)$ and $\lambda(k)$ to correct an image when $\epsilon(k)$ is greater than q comprises:
calculating a $\eta_n(k)$ based on data regarding a $k_1$−n view and a $k_2$+n view, wherein n is an integer;
and correcting an image using the $\eta_n(k)$.

18. A method in accordance with claim 17, wherein n is between 2 and 8 inclusive.

19. A method in accordance with claim 17, wherein n is between 3 and 7 inclusive.

20. A method in accordance with claim 17, wherein n is 5.

21. A method in accordance with claim 7 wherein said estimating a total attenuation $\tau(k)$ using a plurality of projection views comprises estimating a total attenuation $\tau(k)$ in accordance with:

$$\tau(k) = \frac{k_2 - k}{k_2 - k_1}\xi(k_1) + \frac{k - k_1}{k_2 - k_1}\xi(k_2)$$

where $k_1$ and $k_2$ are averages of a plurality of view locations of un-truncated views adjacent to a truncation region comprising at least one projection determined truncated, and $\xi(k)$ is calculated as $$\xi(k) = \sum_{i=1}^{N} p(i, k).$$

22. An imaging apparatus comprising:
a radiation source;
a detector responsive to radiation positioned to receive radiation emitted from said source; and
a computer operationally coupled to said radiation source and said detector, said computer configured to:
calculate a sum of all samples at each projection view of a scan of an object;
determine a maximum value of the calculated sums;
average a plurality of samples m at a projection view index k when the sum of all samples at index k is less than a predetermined percentage of the maximum value;
compare the average to a threshold t;
determine the projection truncated when the average is greater than t; and
determine the projection not truncated when the average is not greater than t.

23. An apparatus in accordance with claim 22 wherein said computer is further configured to compare the average to a threshold t, wherein t is between about 0.25 and about 0.58.

24. An apparatus in accordance with claim 22 wherein said computer is further configured to estimate a total attenuation $\tau(k)$ in accordance with:

$$\tau(k) = \frac{k_2 - k}{k_2 - k_1}\xi(k_1) + \frac{k - k_1}{k_2 - k_1}\xi(k_2)$$

where $k_1$ and $k_2$ are view locations of un-truncated views adjacent to a truncation region comprising at least one projection determined truncated, and $\xi(k)$ is calculated as $$\xi(k) = \sum_{i=1}^{N} p(i, k).$$

25. An apparatus in accordance with claim 22 wherein said computer is further configured to estimate a total attenuation $\tau(k)$ in accordance with:

$$\tau(k) = \frac{k_2 - k}{k_2 - k_1}\xi(k_1) + \frac{k - k_1}{k_2 - k_1}\xi(k_2)$$

where $k_1$ and $k_2$ are averages of a plurality of view locations of un-truncated views adjacent to a truncation region comprising at least one projection determined truncated, and $\xi(k)$ is calculated as $$\xi(k) = \sum_{i=1}^{N} p(i, k).$$

26. An apparatus in accordance with claim 25 wherein said computer is further configured to:
determine a attenuation difference $\lambda(k)$ in accordance with $\lambda(k)=\tau(k)-\xi(k)$
calculate an amount of attenuation to add $\eta(k)$ in accordance with $$\eta(k) = \frac{\pi}{2}R_l^2(k) - x_l(k)p_l(k) - R_l^2(k)\arcsin\left(\frac{x_l(k)}{R_l(k)}\right) + \frac{\pi}{2}R_r^2(k) - x_r(k)p_r(k) - R_r^2(k)\arcsin\left(\frac{x_r(k)}{R_r(k)}\right)$$

where $p_l(k)$, and $P_r(k)$, are the magnitude of a left and a right projection boundary samples averaged over multiple views, respectively, and $x_l(k)$, $x_r(k)$, $R_l(k)$, and $R_r(k)$ are a location and radius of a left and right fitted cylinders, respectfully;
compare $\eta(k)$ to $\lambda(k)$ by calculating a ratio $$\varepsilon(k) = \frac{\eta(k)\mu_w}{\lambda(k)}$$

where $\mu_w$ is an attenuation coefficient of water;
compare $\epsilon(k)$ to a threshold q;
use at least one of $\eta(k)$ and $\lambda(k)$ to correct an image when $\epsilon(k)$ is not greater than q; and
when $\epsilon(k)$ is greater than q:
calculate a $\eta_n(k)$ based on data regarding a $k_1-n$ view and a $k_2+n$ view, wherein n is an integer; and
correct an image using the $\eta_n(k)$.

27. A computer readable medium encoded with a program configured to instruct a computer to:
calculate a sum of all samples at each projection view of a scan of an object;
determine a maximum value of the calculated sums;
average a plurality of samples m at a projection view index k when the sum of all samples at index k is less than a predetermined percentage of the maximum value;
compare the average to a threshold t;
determine the projection truncated when the average is greater than t;
determine the projection not truncated when the average is not greater than
estimate a total attenuation $\tau(k)$ in accordance with $$\tau(k) = \frac{k_2 - k}{k_2 - k_1}\xi(k_1) + \frac{k - k_1}{k_2 - k_1}\xi(k_2)$$

where $k_1$ and $k_2$ are averages of a plurality of view locations of un-truncated views adjacent to a truncation region comprising at least one projection determined truncated, and $\xi(k)$ is calculated as $$\xi(k) = \sum_{i=1}^{N} p(i, k);$$

determine a attenuation difference $\lambda(k)$ in accordance with $\lambda(k)=\tau(k)-\xi(k)$;
calculate an amount of attenuation to add $\eta(k)$ in accordance with $$\eta(k) = \frac{\pi}{2}R_l^2(k) - x_l(k)p_l(k) - R_l^2(k)\arcsin\left(\frac{x_l(k)}{R_l(k)}\right) + \frac{\pi}{2}R_r^2(k) - x_r(k)p_r(k) - R_r^2(k)\arcsin\left(\frac{x_r(k)}{R_r(k)}\right)$$

where $p_l(k)$, and $p_r(k)$, are the magnitude of a left and a right projection boundary samples averaged over multiple views, respectively, and $x_l(k)$, $x_r(k)$, $R_l(k)$, and $R_r(k)$ are a location and radius of a left and right fitted cylinders, respectfully;
compare $\eta(k)$ to $\lambda(k)$ by calculating a ratio $$\varepsilon(k) = \frac{\eta(k)\mu_w}{\lambda(k)}$$

where $\mu_w$ is an attenuation coefficient of water,
compare $\epsilon(k)$ to a threshold q;
use at least one of $\eta(k)$ and $\lambda(k)$ to correct an image when $\epsilon(k)$ is not greater than q; and
when $\epsilon(k)$ is greater than q:
calculate a $\eta_n(k)$ based on data regarding a $k_1-n$ view and a $k_2+n$ view, wherein n is an integer; and
correct an image using the $\eta_n(k)$.

* * * * *

UNITED STATES PATENT AND TRADEMARK OFFICE
CERTIFICATE OF CORRECTION

| | | |
|---|---|---|
| PATENT NO. | : 7,254,259 B2 | Page 1 of 1 |
| APPLICATION NO. | : 10/615411 | |
| DATED | : August 7, 2007 | |
| INVENTOR(S) | : Hsieh et al. | |

It is certified that error appears in the above-identified patent and that said Letters Patent is hereby corrected as shown below:

In Claim 10, column 11, line 48, delete "where p1(k), and" and insert therefor -- where $p_1(k)$, and --.

In Claim 27, column 14, line 18, after "greater than" insert -- t; --.

Signed and Sealed this

First Day of July, 2008

JON W. DUDAS
*Director of the United States Patent and Trademark Office*